United States Patent [19]
Goto et al.

[11] Patent Number: 5,273,978
[45] Date of Patent: Dec. 28, 1993

[54] OPTICALLY ACTIVE ISOINDOLINE DERIVATIVES, THEIR PRODUCTION AND USE

[75] Inventors: Giichi Goto, Osaka; Naohisa Fukuda, Kawanishi, both of Japan

[73] Assignee: Takeda Chemical Industries, Ltd., Osaka, Japan

[21] Appl. No.: 992,004

[22] Filed: Dec. 17, 1992

Related U.S. Application Data

[63] Continuation-in-part of Ser. No. 910,571, Jul. 8, 1992.

[30] Foreign Application Priority Data

Jul. 10, 1991 [JP] Japan ................... 3-169565

[51] Int. Cl.$^5$ .................... A61K 31/40; C07D 209/46
[52] U.S. Cl. ......................... 514/278; 546/122
[58] Field of Search .................. 546/122; 514/278

[56] References Cited

U.S. PATENT DOCUMENTS

| | | | |
|---|---|---|---|
| 4,590,189 | 5/1986 | Hiraga et al. | |
| 4,695,572 | 9/1987 | Goto et al. | 546/122 |
| 4,960,779 | 10/1990 | Bourzat et al. | 546/122 |

OTHER PUBLICATIONS

CA 114(17): 157120j Wada et al. (Mar. 1992).

*Primary Examiner*—Marianne M. Cintins
*Assistant Examiner*—John Peabody
*Attorney, Agent, or Firm*—Wegner, Cantor, Mueller & Player

[57] ABSTRACT

The present invention provides an optically active isoindoline derivative represented by the formula:

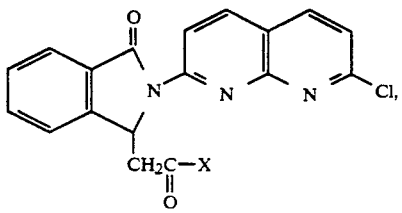

which is useful as an improving, therapeutic and preventive agent for anxiety-associated nervous symptoms, and an intermediate for synthesis thereof.

11 Claims, 2 Drawing Sheets

OPTICALLY ACTIVE ISOINDOLINE DERIVATIVES, THEIR PRODUCTION AND USE

This application is a continuation-in-part of U.S. application Ser. No. 07/910,571 filed Jul. 8, 1992 now pending.

BACKGROUND OF THE INVENTION

The present invention relates to a pharmaceutical, specifically an optically active isoindoline derivative effective in the improvement, treatment or prevention of anxiety-associated nervous symptoms, and an intermediate for synthesis thereof.

In the field of antianxiety drugs, which act on the central nervous system, new compounds having no benzodiazepine skeleton have been investigated. Antianxiety and other drugs acting on the central nervous system must be orally administrable and cause no side effects such as muscular relaxation or sleep induction.

The present inventors conducted investigations and discovered an isoindolinone derivative represented by Formula A, which exhibits excellent antianxiety action, and a pharmacologically acceptable salt thereof (see Japanese Patent Publication Open to Public Inspection No. 69773/1986 corresponding to EP-A-0174858 and U.S. Pat. No. 4,695,572).

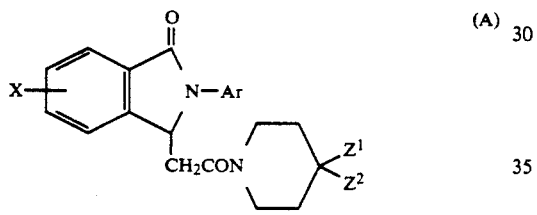
(A)

[wherein X represents hydrogen, halogen or nitro; Ar represents phenyl or naphthyridinyl which may be replaced with a substituent; with respect to $Z^1$ and $Z^2$, either represents hydrogen while the other represents a lower alkanoyloxy or hydroxy, or both represent a lower alkoxy, or both cooperatively represent hydroxyimino, oxo or a group represented by the formula:

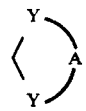

wherein Y represents oxygen or sulfur; A represents a lower alkylene chain which may be branched].

DETAILED DESCRIPTION

Figure 1:
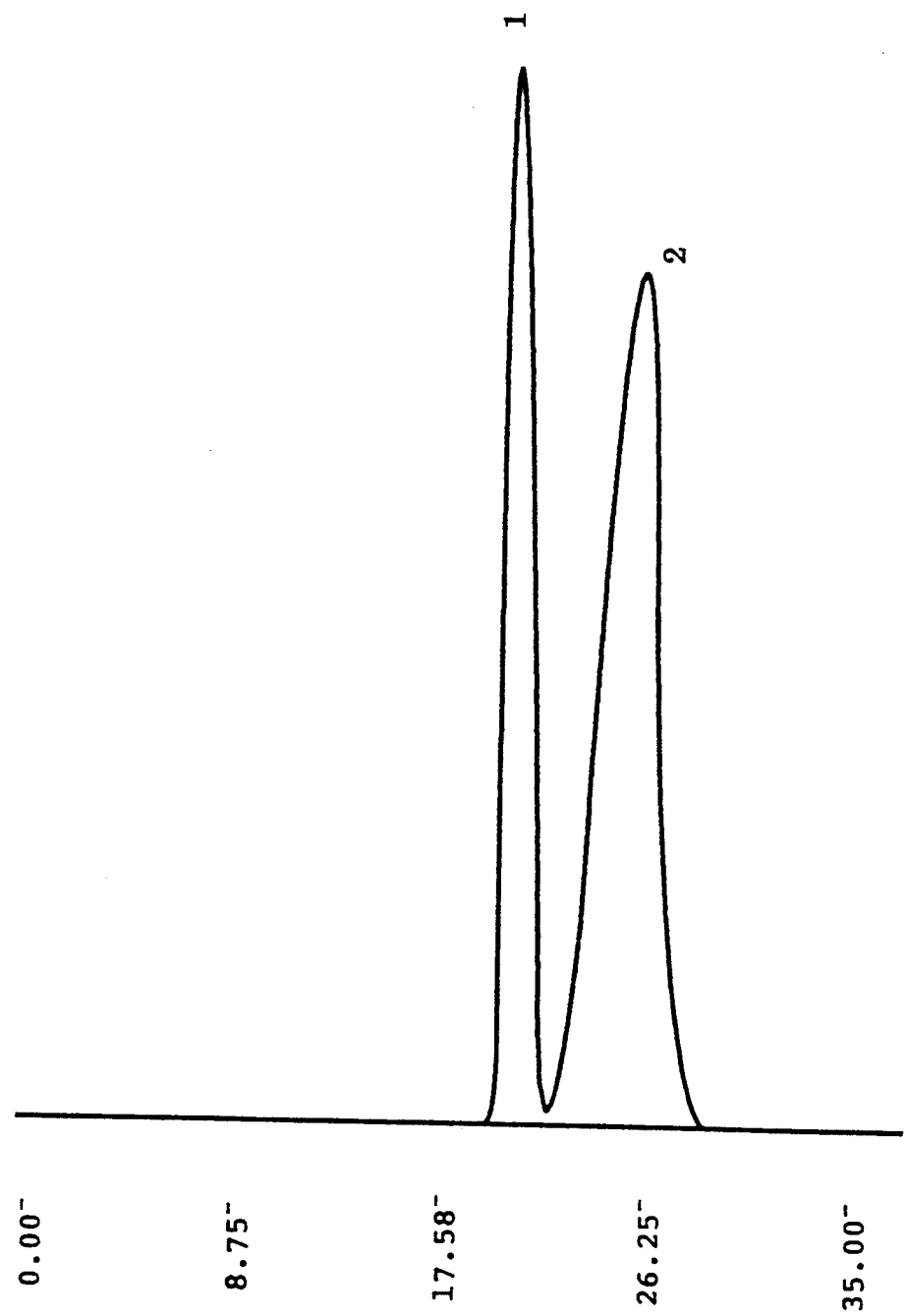
FIG. 1 shows the results of high performance liquid chromatography obtained in the Analytical Example (the racemic modification of the compound of Example 1 used), in which peaks 1 and 2 are for (S)-(+) configuration and (R)-(−) configuration, respectively.

The present inventors investigated in more detail a group of compounds having the following structural formulas II, III and IV, included in the isoindoline derivatives represented by Formula A.

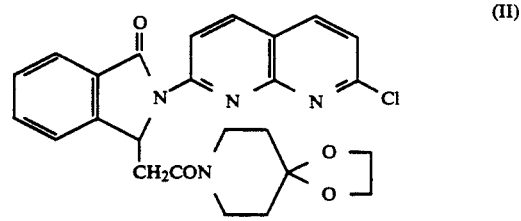

2-(7-chloro-1,8-naphthylidin-2-yl)-3-[(1,4-dioxa-8-azaspiro[4.5]dec-8-yl)carbonylmethyl]isoindolin-1-one

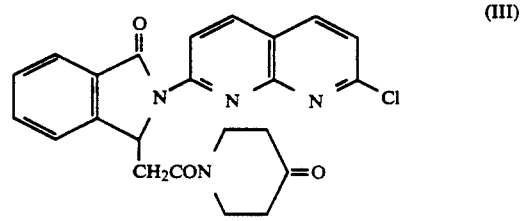

2-(7-chloro-1,8-naphthylidin-2-yl)-3-[(4-piperidon-1-yl)carbonylmethyl]isoindolin-1-one

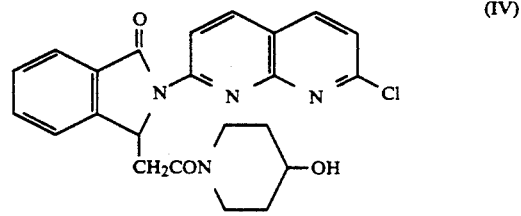

2-(7-chloro-1,8-naphthylidin-2-yl)-3-[(4-hydroxypiperidin-1-yl)carbonylmethyl]isoindolin-1-one The compounds of the above formulas (II), (III) and (IV) each have asymmetric carbon atoms in their molecular structure involving two optical isomers, namely (R) configuration and (S) configuration. Thus, the present inventors conducted detailed investigations of these optical isomers, and found for the first time that, with respect to known compound (A), which possesses antianxiety action, the (S)-(+) configuration alone exhibits excellent antianxiety action.

The present inventors found that an optically active isoindoline derivative represented by the following formula (I') exhibits excellent antianxiety action, i.e., improving, therapeutic and preventive action on anxiety-associated nervous symptoms, and that the (S)-(+)-isoindoline derivative alone possesses bioactivities, while the (R)-(−) configuration has no beneficial bioactivity, the latter being the first such discovery in the field of antianxiety drugs. The inventors conducted further investigations based on these findings, and developed the present invention.

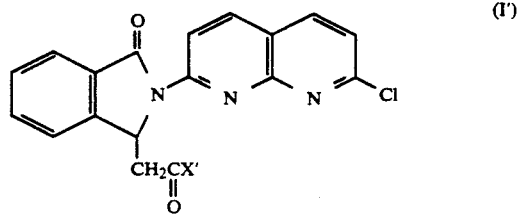

wherein X' represents

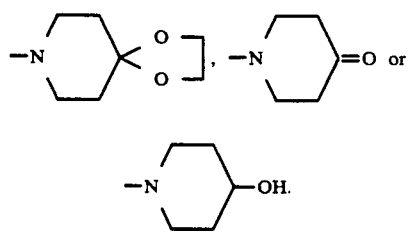

Accordingly, the present invention comprises an optically active isoindoline derivative represented by the formula:

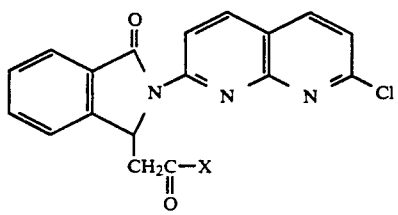 (I)

wherein X represents —OH, a reactive derivative thereof,

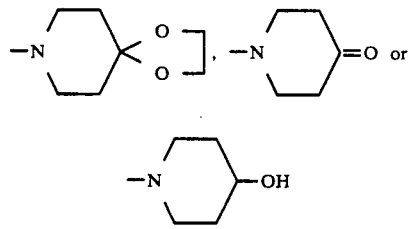

and an improving, therapeutic and preventive agent for anxiety-associated nervous symptoms whose active ingredient is an (S)-(+)-isoindoline derivative represented by the formula:

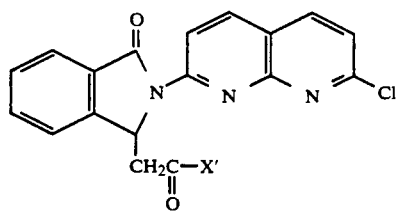 (I')

wherein X' represents

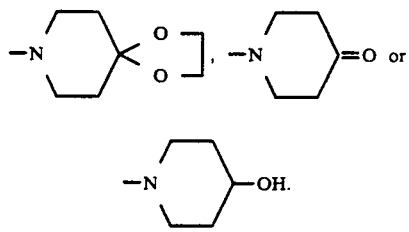

With respect to Formula (I), the compound having —OH or a reactive derivative thereof for X is useful as an intermediate for synthesis of a compound wherein X is

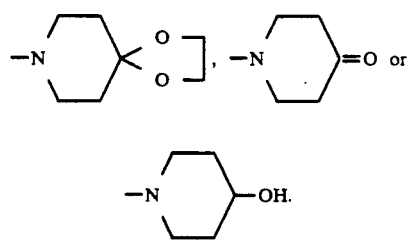

Examples of a reactive derivative of hydroxyl represented by X in the Formula (I) include halogen (e.g. fluorine, chlorine, bromine, iodine; preferably chlorine), lower (C1–4) alkoxy (e.g. methoxy, ethoxy, propoxy, isopropoxy, butoxy) and N-hydroxydiacylimide ester (e.g. N-hydroxysuccinimide ester, N-hydroxyphthalimide ester, N-hydroxy-5-norbornene-2,3-dicarboximide ester), with preference given to halogen.

The (S)-(+)-isoindoline derivative of the present invention is a compound represented by the following formula (V):

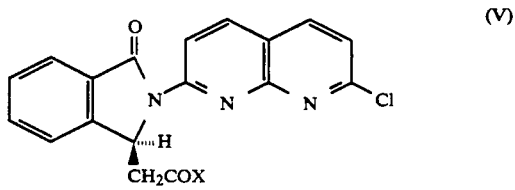 (V)

wherein X represents —OH, a reactive derivative thereof,

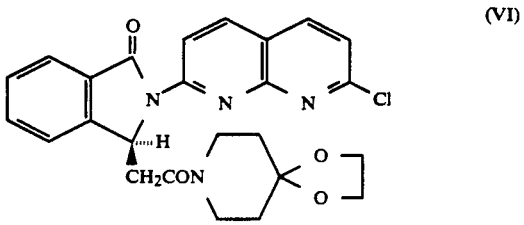

More specifically, the bioactive compound of the present invention can be represented by the following formulas (VI, VII and VIII).

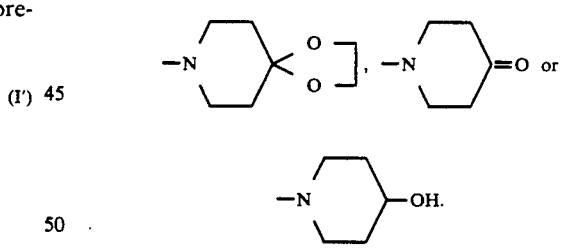 (VI)

(S)-(+)-2-(7-chloro-1,8-naphthylidin-2-yl)-3-[(1,4-dioxa-8-azaspiro[4.5]dec-8-yl)carbonylmethyl]isoindolin-1-one

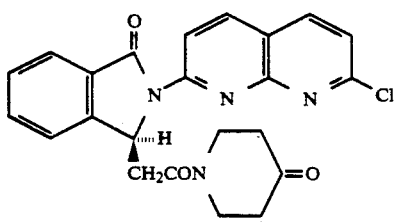

(S)-(+)-2-(7-chloro-1,8-naphthylidin-2-yl)-3-[(4-piperidon-1-yl)-carbonylmethyl]isoindolin-1-one

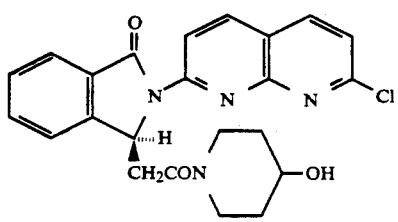

(S)-(+)-2-(7-chloro-1,8-naphthylidin-2-yl)-3-[(4-hydroxypiperidin-1-yl)carbonylmethyl]isoindolin-1-one

METHOD FOR PRODUCTION

The optically active (S)-(+)-isoindoline derivative (V), a compound of the present invention, can be obtained by resolving the racemic modification isoindoline-3-acetate intermediate (IX) by a known method to yield an optically active (S)-(+)-isoindoline-3-acetate intermediate (X) and, if necessary, converting the compound (X; X=hydroxyl) into a compound (X'; X=a reactive derivative of hydroxyl) by a known method, and subsequently amidating the compound (X or X') by a known method (e.g., the method described in Japanese Patent Publication Open to Public Inspection No. 69773/1986 corresponding to U.S. Pat. No. 4,695,572).

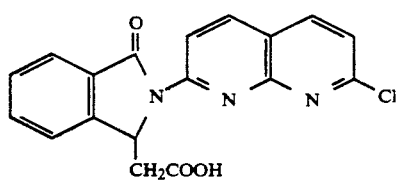

↓ Resolution

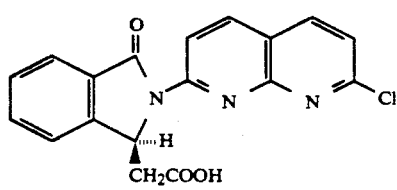

↓ Amidation

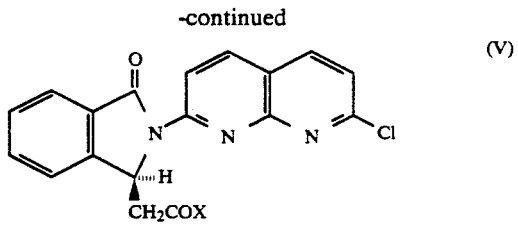

The racemic modification isoindoline-3-acetate intermediate (IX) can be synthesized by the method described in Japanese Patent Publication Open to Public Inspection No. 69773/1986 corresponding to U.S. Pat. No. 4,695,572. It can be optically resolved by the typical method described below.

(1) The method in which a salt with an optically active amine, such as (+)-cinchonine or (−)-cinchonidine, (−)-quinine, (−)-brucine, (+)-ephedrine or (−)-ephedrine, (+)-lysine, (+)-dehydroabietylamine, (+)- or (−)-α-methylbenzylamine, (+)- or (−)-α-methyl-p-nitrobenzylamine, (+)- or (−)-1-(1-naphthyl)ethylamine, (+)- or (−)-(cis-2-benzylaminocyclohexyl)methanol, (+)- or (−)-α-phenylglycine or (+)-tyrosine hydrazide, is formed and fractionally recrystallized from an appropriate solvent and then treated with acid (e.g., hydrochloric acid, sulfuric acid, nitric acid, phosphoric acid), to yield a free acid (X).

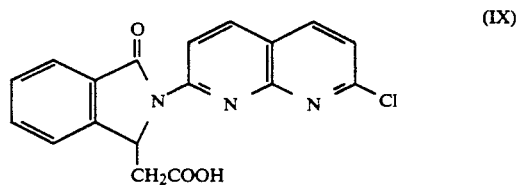

↓ *Z

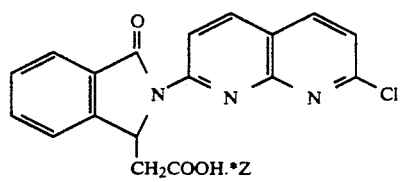

↓ Fractional recrystallization

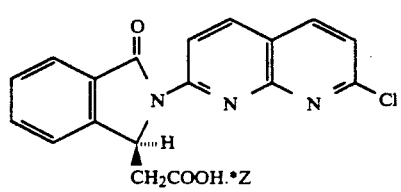

↓ (H)+

(In the above formulas, *Z represents an optically active amine).

(2) The method using a chiral column to resolve the racemic modification.

(3) The method in which the racemic modification (IX) is converted to an ester of an optically active alcohol, which is then separated by fractional recrystallization or silica gel column chromatography, to yield an optically active ester, which is then separated by deesterification with acid.

(IX)

↓ *R—OH

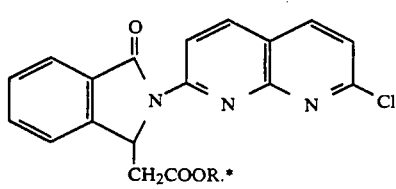

CH₂COOR.*

↓ Fractional recrystallization or column chromatography

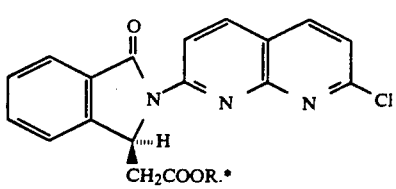

CH₂COOR.*

↓ (H)⁺

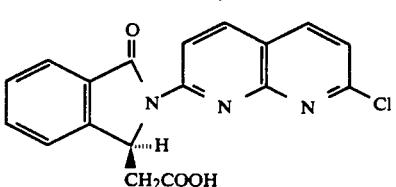

(X)

(In the above formulas, *ROH represents an optically active alcohol).

Examples of optically active alcohols preferred for this method include l-methol and (+)- or (−)-α-methylbenzyl alcohol.

The optically active isoindoline derivative of the present invention can also be produced by resolving the racemic modification thereof using a chiral column.

The pharmacological action of the optically active isoindoline derivative (V) of the present invention is described below.

BIOCHEMICAL EXPERIMENT

The affinity of the compound of the present invention to a benzodiazepine receptor was investigated using radioactive [$^3$H] diazepam.

Capability of specific binding to a benzodiazepin receptor was determined in accordance with the method described in the literature (Nature, 266, 732 (1977); European J. Pharmacol., 48, 263 (1978). Specifically, a crude mitochondrial fraction obtained from the cerebral cortex of male SD rats at 9 to 10 weeks of age was suspended in 50 mM Tris-HCL buffer (pH 7.4), and incubated, together with several concentrations of the subject drug and $^3$H-diazepam (final concentration 2 nM), at 4° C. for 20 minutes. This suspension was then filtered through a Whatman GF/B glass fiber filter, and the $^3$H-diazepam radioactivity on the filter was measured using a liquid scintillation counter. The concentration of the subject drug at which $^3$H-diazepam binding was inhibited by 50% was taken as the IC$_{50}$ value.

Results from a typical compounds (VI) and (VIII) of the present invention and the corresponding racemic modifications thereof are shown in Table 1.

TABLE 1

| Compound | IC$_{50}$ (nM) |
| --- | --- |
| (VI) | 0.320 |
| Racemic modification | 0.380 |
| (VIII) | 0.92 |
| Racemic modification | 2.14 |

As is evident from these results, the resolution product (VI) had no enhanced affinity to the benzodiazepin receptor, because the racemic modification itself already possesses nearly fully potent action.

PHARMACOLOGICAL EXPERIMENT

The antianxiety action of the compound of the present invention was investigated.

Antianxiety Action

Antianxiety action was assessed, in accordance with the method of Vogel et al. Psychopharmacologia, 21, 1 (1970), as follows. An apparatus, comprising a large transparent box with a stainless steel lattice floor and a small dark opaque box with a water drinking port, was set so that the subject animals' feet were electrically stimulated via the lattice floor once per 20 times of water drinking. Male rats (SD/JCL), denied water for 48 hours, were orally dosed with the subject compound. 30 minutes later, each animal was placed in the apparatus; water drinking frequency in 3 minutes was counted, and the rate of increase from the water drinking frequency in the physiological saline dosed group was calculated for an index of intensity of antianxiety action to determine the minimum effective dose.

Compounds (VI) and (VIII), typical among the compounds (V) of the present invention, and the corresponding racemic modifications thereof were compared as to antianxiety action. The results are shown in Table 2.

TABLE 2

| Testing Item | Minimum Effective Dose (MED) of the Compounds (VI) and (VIII) of the Present Invention | Minimum Effective Dose (MED) of the Corresponding Racemic Modifications |
| --- | --- | --- |
| Antianxiety action (Vogel method) of (VI) | 1.25 mg/kg, p.o. | 10 mg/kg, p.o. |
| Antianxiety action (Vogel method) of (VIII) | 5.0 mg/kg, i.p. | 20 mg/kg, i.p. |

As seen in Table 2, the antianxiety action of compounds (VI) and (VIII) of the present invention was, surprisingly, 8 times and 4 times stronger than that of the corresponding racemic modifications, respectively. These finding cannot be expected from the common idea of racemic modification resolution products, nor from the action on a benzodiazepin receptor shown in Table 1.

Compound (V) of the present invention acts on the central nervous system of mammals. It possesses a high capability of specific binding to benzodiazepine receptors and exhibits strong antianxiety action in anticonflict experiments in rats. The minimum lethal dose (MLD) of the compound of the present invention in rats is over 1000 mg/kg (P.O.), much higher than the minimum effective dose (MED), indicating a very wide range of drug safety. For example, the MED of compound (VI) for antianxiety action in rats is 1.25 mg/kg (P.O.) or lower.

Compound (V) of the present invention, in comparison with the racemic modification isoindolinone derivative described above and the currently commercially available antianxiety benzodiazepin drugs, has a wider range of drug safety, separation of action from hypnotic action, muscular relaxation action and other side effects is very good, the sleepiness, dizziness and similar side effects are very slight, and its oral administration offers a marked effect; it is useful as an antianxiety drug in humans and other mammalians.

Diseases against which the compound of the present invention is effective include various psychosomatic diseases and anxiety syndromes, such as autonomic imbalance, nervous vomiting, nervous dermatitis, alopecia areata, nervous angina pectoris and nervous dyspnea; the compound of the present invention can be used to prevent or treat these diseases. The compound of the present invention also exhibits antispasmodic action. It can therefore also be used to treat epilepsy and traumatic spasm, for instance.

The compound of the present invention is, for example, administered to humans and other mammalians orally or parenterally in various dosage forms, including tablets, granules, capsules, injections and suppositories. Although dose quantity varies depending on the target disease, symptoms and other factors, it is normally 0.01 mg to 100 mg, preferably 0.05 mg to 10 mg daily in oral administration for adults.

EXAMPLES

The present invention is hereinafter described in more detail by means of the following working examples, analytical example and preparation example, which are not to be construed as limitative.

The powder X-ray diffractions in Examples were measured by use of the model of Rigaku RINT System and Cu.Ka as X-ray soursce at the condition of 40 KV and 40 mA.

EXAMPLE 1

(S)-(+)-2-(7-chloro-1,8-naphthylidin-2yl)-3-[(1,4-dioxa-8-azaspiro[4.5]dec-8-yl)carbonylmethyl]isoindolin-1-one

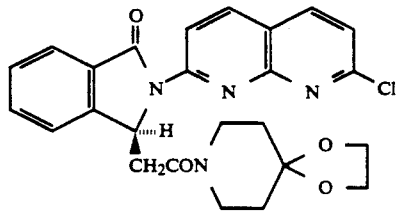

(1)
(S)-(+)-2-(7-chloro-1,8-naphthylidin-2-yl)-1-oxoisoindolin-3-acetic acid.(+)-cinchonine salt

8.10 g of 2-(7-chloro-1,8-naphthylidin-2-yl)-1-oxoisoindolin-3-acetic acid and 6.73 g of (+)-cinchonine were dissolved in 250 ml of methanol with heating. Subsequently, the solution was heated to the extent that no crystal separation occurred to distill off the methanol. After 100 ml of hot acetone was added to the residue, the reaction broth was kept standing at room temperature. One day later, the precipitated tabular crystals were collected by filtration and washed with a small amount of acetone. The mother liquor and the washings were combined and heated to concentrate. The resulting oily substance was dissolved in 60 ml of acetone with heating, and the resulting solution was kept standing at room temperature. One day later, the precipitated needle crystals were collected by filtration and washed with a small amount of acetone. These crystals were then dissolved in hot acetone, and the resulting solution was kept standing at room temperature for recrystallization to yield 3.7 g of pure (S)-(+)-2-(7-chloro-1,8-naphthylidin-2-yl)-1-oxoisoindolin-3-acetic acid.(+)-cinchonine salt.

Melting point: 207°–208° C. (needles)

$[\alpha]_D^{24} + 200°$ (c=1.0, methanol)

Elemental analysis (for $C_{18}H_{12}ClN_3O_3 \cdot C_{19}H_{22}N_2O$): Calculated: C: 68.56; H: 5.29; N: 10.80. Found: C: 68.71; H: 5.28; N: 10.77.

(2)   (S)-(+)-2-(7-chloro-1,8-naphthylidin-2-yl)-1-oxoisoindolin-3-acetic acid

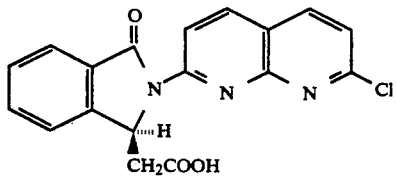

3.5 g of the cinchonine salt obtained in (1) above was dissolved in 30 ml of methanol. To the resulting solution, 40 ml of 3N aqueous hydrochloric acid was added. The precipitated crystals were collected by filtration and washed with water. After drying, the crystals were recrystallized from methanol to yield 1.8 g of (S)-(+)-2-(7-chloro-1,8-naphthylidin-2-yl)-1-oxoisoindolin-3-acetic acid.

Melting point: 197°–198° C., 269°–272° C. (decomposed) (double melting point)

$[\alpha]_D^{24} + 142°$ (c=0.2, methanol)

Elemental analysis (for $C_{18}H_{12}ClN_3O_3$): Calculated: C: 61.11; H: 3.42; N: 11.88. Found: C: 61.04; H: 3.44; N: 11.86.

(3) To a dimethylformamide solution (15 ml) of 1.77 g of the (S)-(+)-2-(7-chloro-1,8-naphthylidin-2-yl)-1-oxoisoindolin-3-acetic acid obtained in (2) above, 0.77 g of 1,4-dioxa-8-azaspiro[4.5]decane, 0.56 g of triethylamine and 0.98 g of diethyl cyanophosphate were added, in that order, while stirring the solution with ice cooling. After the reaction broth was stirred with ice cooling for 30 minutes, 100 ml of water was added, and the precipitated crystals were collected by filtration and washed with water. After drying, the crystals were recrystallized from dichloromethane-ethyl acetate (1:3) to yield 1.92 g of the desired compound.

Melting point: 208°–209° C. (plates)

$[\alpha]_D^{24} + 97.5°$ (c=1.0, chloroform)

Elemental analysis (for $C_{25}H_{23}ClN_4O_4$): Calculated: C: 62.70; H: 7.84; N: 11.70. Found: C: 62.76; H: 4.88; N: 11.65.

(4) The crystals thus obtained were identified by subjecting them to determination by means of powder X-ray diffraction.

The result of powder X-ray diffraction is shown by Distance Value and Diffraction Intensity (S: strong, M: middle, W: weak): B-form crystal

| D value (Å) | 11.7 | 5.8 | 5.5 | 5.4 | 5.3 | 5.2 | 4.79 | 4.58 | 4.52 | 4.46 | 4.37 | 4.25 | 4.06 | 3.99 | 3.88 | 3.45 | 3.26 |
|---|---|---|---|---|---|---|---|---|---|---|---|---|---|---|---|---|---|
| Intensity | W | M | W | M | W | W | M | W | W | W | M | W | S | W | M | M | M |

EXAMPLE 2

(S)-(+)-2-(7-chloro-1,8-naphthylidin-2-yl)-3-[(4-piperidon-1-yl)carbonylmethyl]isoindolin-1-one

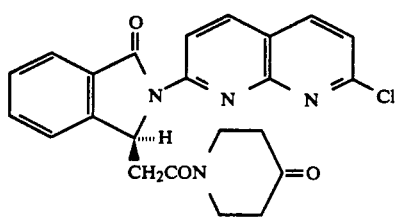

In the same manner as in Example 1 (3), the desired compound (1.38 g) was obtained from (S)-(+)-2-(7-chloro-1,8-naphthylidin-2-yl)-1-oxoisoindolin-3-acetic acid (1.3 g) and 4-piperidone monohydrate monohydrochloride (0.7 g).

Melting point: 292°–294° C. (needles)

$[\alpha]_D^{23} + 117°$ (c=0.5, chloroform)

Elemental analysis (for $C_{23}H_{19}ClN_4O_3$): Calculated: C: 63.52; H: 4.40; N: 12.88. Found: C: 63.60; H: 4.39; N: 12.75.

EXAMPLE 3

(S)-(+)-2-(7-chloro-1,8-naphthylidin-2-yl)-3-[(4-hydroxypiperidin-1-yl)carbonylmethyl]isoindolin-1-one

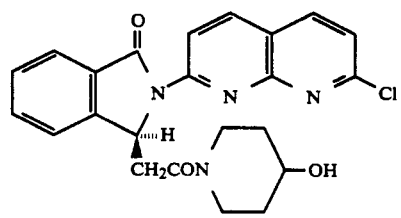

In the same manner as in Example 1 (3), the desired compound (1.33 g) was obtained from (S)-(+)-2-(7-chloro-1,8-naphthylidin-2-yl)-1-oxoisoindolin-3-acetic acid (1.26 g) and 4-hydroxypiperidine (0.79 g).

Melting point: 264°–266° C. (needles)

$[\alpha]_D^{24} + 143.8°$ (c=1.0, chloroform)

Elemental analysis (for $C_{23}H_{21}ClN_4O_3$): Calculated: C: 63.23; H: 4.84; N: 12.82. Found: C: 63.10; H: 4.78; N: 12.87.

EXAMPLE 4

(R)-(−)-2-(7-chloro-1,8-naphthylidin-2-yl)-3-[(1,4-dioxa-8-azaspiro[4.5]dec-8-yl)carbonylmethyl]isoindolin-1-one

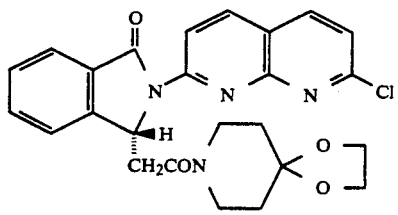

(1) (R)-(+)-2-(7-chloro-1,8-naphthylidin-2-yl)-1-oxoisoindolin-3-acetic acid.(+)-cinchonine salt

The former tabular crystals obtained in Example 1 (1) were recrystallized from methanol-acetone (1:3) to yield 4.1 g of a pure (R)-(+) salt.

Melting point: 156°–160° C. (plates)
$[\alpha]_D^{24}+0.7°$ (c=1.0, methanol)
Elemental analysis (for $C_{18}H_{12}ClN_3O_3 \cdot C_{19}H_{22}N_2O$):
Calculated: C: 68.56; H: 5.29; N: 10.80. Found: C: 68.66; H: 5.34; N: 10.73.

(2) (R)-(−)-2-(7-chloro-1,8-naphthylidin-2-yl)-1-oxoisoindolin-3-acetic acid

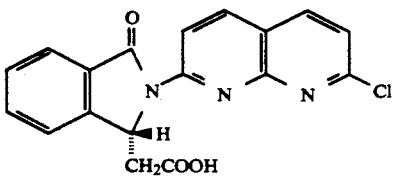

3.9 g of the cinchonine salt obtained in (1) above was treated in the same manner as in Example 1 (2) to yield 2.1 g of an (R)-(−) carboxylic acid.
Melting point: 197°–198°, 269°–272° C. (decomposed) (double melting point)
$[\alpha]_D^{24}-142°$ (c=0.2, methanol)
Elemental analysis (for $C_{18}H_{12}ClN_3O_3$): Claculated: C: 61.11; H: 3.42; N: 11.88. Found: C: 61.09; H: 3.41; N: 11.90.

(3) 1.86 g of the (R)-(−) carboxylic acid obtained in (2) above was reacted with 0.86 g of 1,4-dioxa-8-azaspiro[4.5]decane, 0.63 g of triethylamine and 1.0 g of diethyl cyanophosphate in the same manner as in Example 1 (3), and then treated to yield 2.06 g of the desired compound.
Melting point: 207°–208° C. (plates)
$[\alpha]_D^{24}-97.4°$ (c=1.0, chloroform)
Elemental analysis (for $C_{25}H_{23}ClN_4O_4$): Calculated: C: 62.70; H: 4.84; N: 11.70. Found: C: 62.71; H: 4.81; N: 11.72.

EXAMPLE 5

(S)-(+)-2-(7-chloro-1,8-naphthylidin-2-yl)-3-[(1,4-dioxa-8-azaspiro[4.5]dec-8-yl)carbonylmethyl]isoindolin-1-one

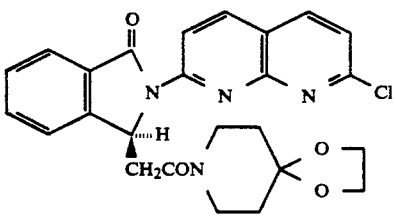

1.85 g of the (S)-(+) carboxylic acid obtained in Example 1 (2) was suspended in 15 ml of 1,2-dichloroethane. To this suspension, 0.1 ml of dimethylformamide (DMF) and 3 ml of thionyl chloride were added, followed by stirring at 45° C. for 3 to 4 hours. After cooling, the excess thionyl chloride and 1,2-dichloroethane were distilled off under reduced pressure. The resulting (S)-(+) acid chloride was used for the following reaction as such, without purification.

The above (S)-(+) acid chloride was suspended in 10 ml of dichloromethane. To this suspension, a solution of 0.85 g of 1,4-dioxa-8-azaspiro[4.5]decane and 0.6 g of triethylamine in 4 ml of dichloromethane was added drop by drop. After stirring for 30 minutes, water was added, and the dichloromethane layer was separated. The dichloromethane layer was washed with water and dried over anhydrous sodium sulfate, after which the dichloromethane was distilled off, to yield a crude crystal, which was recrystallized from dichloromethane-ethyl acetate (1:3) to yield 1.76 g of the desired compound.

ANALYTICAL EXAMPLE

The compound of Example 1, typical among the compounds of the present invention, and the racemic modification thereof, were analyzed by high performance liquid chromatography using an optical resolution column.

Analytical Conditions

Figure 2:
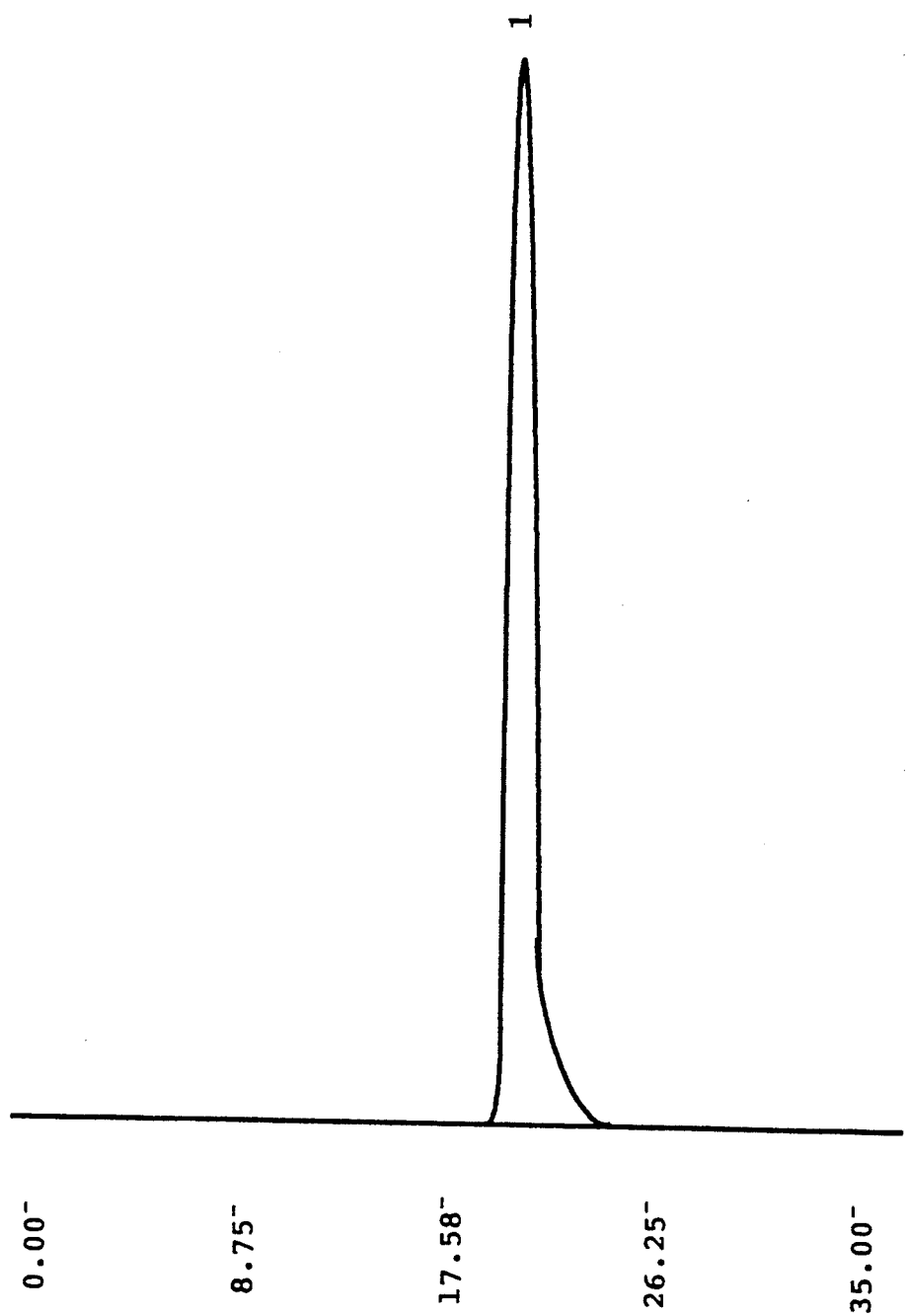
FIG. 2 shows the results of high performance liquid chromatography obtained in the Analytical Example (the compound of Example 1 used), in which peak 1 is the peak for (S)-(+) configuration.

Column: Chiral Cell OJ (4.6×250 mm)
Mobile phase: n-hexane-2-propanol-ethanol (10:1:1, v/v)
Flow rate: 1 ml/min
Detection: UV 344 nm
The analytical results are shown in FIGS. 1 and 2.

EXAMPLE 6

C-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one In 60 ml of dichloromethane was dissolved 20 g of B-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one obtained in substantially the same manner as described in Example 1 (3). The solution was concentrated under reduced pressure to leave crystals, which were subjected to drying in vacuo at 60° C. to afford 19.2 g of C-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one, m.p. 193°–195° C. (needles).

| Powder X-ray diffraction: | | | | | | | | | | |
|---|---|---|---|---|---|---|---|---|---|---|
| D value (Å) | 10.9 | 7.2 | 6.4 | 5.3 | 4.11 | 4.03 | 3.71 | 3.57 | 3.42 | 3.23 | 2.84 |
| Intensity | W | W | M | S | M | M | W | W | W | M | W |

EXAMPLE 7

D-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one In 300 ml of water was suspended 10 g of C-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one obtained in Example 6. The suspension was stirred for 2 hours at room temperatures. Resultant crystals were collected by filtration and washed with water to afford about 12 g of D-form crystals (needles) of (S)-(+)-2-(7-chloro-1,8-naphthylidin-2-yl)-3-[(1,4-dioxa-8-azaspiro[4,5]dec-8-yl)carbonylmethyl]isoindolin-1-one as wet crystals.

The crystals thus obtained were identified as those of monohydrate by subjecting them to determination by means of thermobalance and powder X-ray.

| Powder X-ray diffraction: | | | | | | | | | | | |
|---|---|---|---|---|---|---|---|---|---|---|---|
| D value (Å) | 9.2 | 7.5 | 5.4 | 5.1 | 4.51 | 4.05 | 3.87 | 3.75 | 3.54 | 3.53 | 3.18 | 3.03 |
| Intensity | W | W | W | M | M | M | M | M | M | W | M | W |

EXAMPLE 8

A-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one About 10 g of the wet crystals of D-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one obtained in Example 7 was subjected to drying in vacuo at 80 C. to afford 8.2 g of A-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one, m.p. 203°-204° C. (needles).

| Powder X-ray diffraction: | | | | | | | | | | | | | | |
|---|---|---|---|---|---|---|---|---|---|---|---|---|---|---|
| D value (Å) | 10.6 | 9.2 | 7.4 | 7.1 | 5.9 | 5.1 | 5.0 | 4.58 | 4.34 | 4.18 | 4.10 | 3.73 | 3.54 | 3.36 | 3.15 |
| Intensity | W | W | W | M | M | S | M | M | W | W | M | W | M | M | W |

EXAMPLE 9

E-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one 10 g of B-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one obtained in substantially the same manner as described in Example 1 (3) was dissolved in 30 ml of dimethylformamide under heating. This solution was added dropwise to 250 ml of ethanol at temperatures ranging from 2° to 3° C. The mixture was stirred for one hour at temperatures ranging from 0° to 5° C. Resultant crystals were collected by filtration and subjected to drying in vacuo at 80° C. to afford 8.6 g of E-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one, m.p. 192°-194° C. (needles).

| Powder X-ray diffraction: | | | | | | | | | | |
|---|---|---|---|---|---|---|---|---|---|---|
| D value (Å) | 12.8 | 5.1 | 4.98 | 4.77 | 4.54 | 4.34 | 4.07 | 3.92 | 3.36 | 3.19 | 2.99 |
| Intensity | W | M | M | M | M | S | M | W | W | W | M |

EXAMPLE 10

Transformation of C-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one into B-form crystals In 10 ml of ethanol was suspended 2 g of C-form crystals of (S)-(+)-2-(7-chloro-1,8-naphthylidin-2-yl)-3-[1,4-dioxa-8-yl)carbonylmethyl]isoindolin-1-one obtained in Example 6. The suspension was stirred for 10 minutes at room temperature. Resultant crystals were collected by filtration and dried at 80° C. in vacuo to afford 1.6 g of B-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one, m.p. 208°-209° C. (plates).

EXAMPLE 11

Transformation of D-form crystals of (S)-(+)-2-(7-chloro-1,8-naphthylidin-2-yl)-3-[(1,4-dioxa-8-azaspiro[4,5]dec-8yl)carbonylmethyl]isoindolin-1-one into B-form crystals In 10 ml of ethanol was suspended about 2 g of the wet crystals of C-form crystals of (S)-(+)-2-(7-chloro-1,8-naphthylidin-2-yl)-3[(1,4-dioxa-8-azaspiro[4,5]dec-8-yl)carbonylmethyl]isoindolin-1-one obtained in Example 7. The suspension was stirred for 10 minutes at room temperature. Resultant crystals were collected by filtration and dried at 80 C. in vacuo to afford 1.2 g of B-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one, m.p. 208°-209° C., m.p. 208°-209° C. (plates).

EXAMPLE 12

Transformation of A-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one into B-form crystals In 10 ml of ethanol was suspended 2 g of A-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one obtained in Example 8. The suspension was stirred for 10 minutes at room temperature. Resultant crystals were collected by filtration and dried at 80° C. in vacuo to afford 1.7 g of B-form crystals of (S)-(+)-2-(7-chloro-1,8-naphthylidin-2-yl)-3-[(1,4-dioxa-8-azaspiro [4,5]dec-8-yl)carbonylmethyl]isoindolin-1-one, m.p. 208°-209° C. (plates).

EXAMPLE 13

Transformation of E-form crystals of (S)-(+)-2-(7-chloro-1,8-naphthylidin-2-yl)-3-[(1,4-dioxa-8-azaspiro[4,5]dec-8-yl)carbonylmethyl]isoindolin-1one into B-form crystals In 10 ml of ethanol was suspended 2 g of E-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one obtained in Example 9. The suspension was stirred for 10 minutes at room temperature. Resultant crystals were collected by filtration and dried at 80° C. in vacuo to afford 1.7 g of B-form crystals of (S)-(+)-2-(7-chloro-1,8-naphthylidin-2-yl)-3-[(1,4-dioxa-8-azaspiro [4,5]dec-8-yl)carbonylmethyl]isoindolin-1-one, m.p. 208°-209° C. (plates).

EXAMPLE 14

Transformation of A-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one into D-form crystals In 10 ml of water was suspended 2 g of A-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one obtained in Example 8. The suspension was stirred for 10 minutes at room temperature. Resultant crystals were collected by filtration to afford about 2.2 g of wet D-form crystals of (S)-(+)-2-(7-chloro-1,8-naphthylidin-2-yl)-3-[(1,4-dioxa-8-azaspiro[4,5]dec-8-yl)carbonylmethyl]isoindolin -1-one.

EXAMPLE 15

Transformation of E-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one into D-form crystals In 10 ml of water was suspended 2 g of E-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one obtained in Example 9. The suspension was stirred for 10 minutes at room temperature. Resultant crystals were collected by filtration to afford about 2.3 g of wet D-form crystals of (S)-(+)-2-(7-chloro-1,8-naphthylidin-2-yl)-3-[(1,4-dioxa-8-azaspiro[4,5]dec-8-yl)carbonylmethyl]isoindolin-1-one.

PREPARATION EXAMPLE 1

| | |
|---|---|
| (1) (S)-(+)-2-(7-chloro-1,8-naphthylidin-2-yl)-3-[(1,4-dioxa-8-azaspiro[4.5]dec-8-yl)carbonylmethyl]isoindolin-1-one | 1 g |
| (2) Lactose | 89 g |
| (3) Corn starch | 29 g |
| (4) Magnesium stearate | 1 g |

(1), (2) and 15 g of corn starch were mixed; this mixture, together with a paste prepared from 8 g of corn starch, was then granulated. To these granules, 6 g of corn starch and (4) were added. The resulting mixture was compressed with a compressive tableting machine to yield 1000 tablets of 5 mm diameter containing 1 mg of (1) per tablet.

What is claimed is:

1. An optically active (S)-isoindoline derivative represented by the formula:

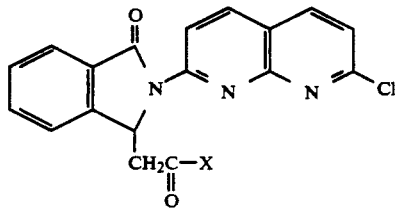

wherein X represents —OH, a reactive derivative thereof,

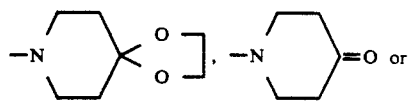

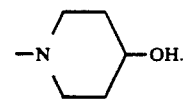

2. The optically active compound of claim 1 which is an (S)-(+)-2-(7-chloro-1,8-naphthylidin-2-yl)-3-[(1,4-dioxa-8-azaspiro[4.5]dec-8-yl)carbonylmethyl]isoindolin-1-one.

3. The optically active compound of claim 1 which is an (S)-(+)-2-(7-chloro-1,8-naphthylidin-2-yl)-3-[(4-piperidon-1-yl)carbonylmethyl]isoindolin-1-one.

4. The optically active compound of claim 1 which is an (S)-(+)-2-(7-chloro-1,8-naphthylidin-2-yl)-3-[(4-hydroxypiperidin-1-yl)carbonylmethyl]isoindolin-1-one.

5. The compound of claim 2 wherein the compound is a B-form crystal.

6. A therapeutic and preventive agent for treating anxiety-associated nervous symptoms comprising an effective amount of an (S)-(+)isoindoline derivative represented by the formula:

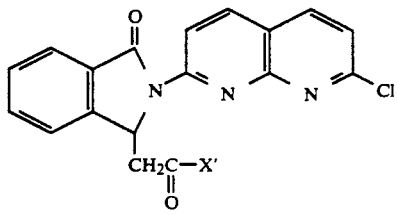

wherein X' represents

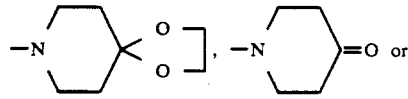

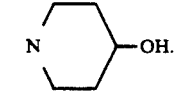

7. The therapeutic and preventive agent for anxiety-associated nervous symptoms of claim 6 comprising an effective amount of an (S)-(+)-2-(7-chloro-1,8-naphthylidin-2-yl)-3-[(1,4-dioxa-8-azaspiro[4.5]dec-8-yl)carbonylmethyl]isoindolin-1-one.

8. The therapeutic and preventive agent for anxiety-associated nervous symptoms of claim 6 comprising an effective amount of an (S)-(+)-2-(7-chloro-1,8-naphthylidin-2-yl)-3-[(4-piperidon-1-yl]carbonylmethyl]isoindolin-1-one.

9. The therapeutic and preventive agent for anxiety-associated nervous symptoms of claim 6 comprising an effective amount of an (S)-(+)-2-(7-chloro-1,8-naphthylidin-2-yl)-3-[(4-hydroxypiperidin-1-yl]carbonylmethyl]isoindolin-1-one.

10. The agent of claim 7 prepared from the B-form crystal of (S)-(+)-2-(7-chloro-1,8-naphthylidin-2-yl)-3-[(1,4-dioxa-8-azaspiro[4.5]dec-8-yl)carbonymethyl-]isoindolin-1-one.
11. A method for treating anxiety-associated symptoms of a mammal, which comprises administering to said mammal an effective amount of an (S)-(+)-compound represented by the formula:
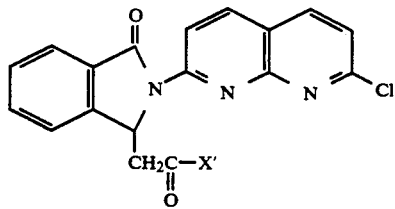
wherein X' represents
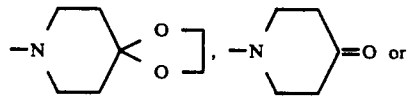
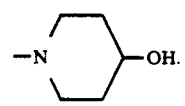
* * * * *